United States Patent [19]

Su

[11] Patent Number: 5,206,381

[45] Date of Patent: Apr. 27, 1993

[54] ULTRAVIOLET RADIATION CURABLE POLYAMIDEIMIDE OLIGOMERS

[75] Inventor: Wei-Fang A. Su, Murrysville Boro, Pa.

[73] Assignee: Westinghouse Electric Corp., Pittsburgh, Pa.

[21] Appl. No.: 728,811

[22] Filed: Jul. 11, 1991

Related U.S. Application Data

[63] Continuation of Ser. No. 390,123, Aug. 7, 1989, abandoned.

[51] Int. Cl.[5] .................................... C07D 209/48
[52] U.S. Cl. .................................................. 548/476
[58] Field of Search ....................................... 548/476

[56] References Cited

U.S. PATENT DOCUMENTS

| | | | |
|---|---|---|---|
| 3,518,230 | 6/1970 | Sheffer | 528/73 |
| 3,541,038 | 11/1970 | Natano | 524/726 |
| 3,562,217 | 2/1971 | Zalewski et al. | 528/73 |
| 3,578,639 | 5/1971 | Schaffer | 428/379 |
| 3,608,054 | 9/1971 | Alvino | 264/309 |
| 3,652,471 | 3/1972 | Sattler | 524/323 |
| 3,732,186 | 5/1973 | Dunwald et al. | 428/425.8 |
| 3,843,587 | 10/1974 | Keating et al. | 428/383 |
| 3,892,768 | 7/1975 | Alvino et al. | 548/433 |
| 3,984,375 | 10/1976 | Frost | 361/26 |
| 4,069,209 | 1/1978 | Lange | 528/289 |
| 4,113,706 | 9/1978 | Lange | 528/289 |
| 4,117,032 | 9/1978 | Kwiecinski | 528/273 |
| 4,195,159 | 3/1980 | Kwiecinski | 528/288 |
| 4,206,098 | 6/1980 | Sattler et al. | 428/458 |
| 4,214,071 | 7/1980 | Alvino et al. | 528/222 |
| 4,317,858 | 3/1982 | Sattler | 525/423 |
| 4,379,879 | 4/1983 | Okada et al. | 524/186 |
| 4,420,535 | 12/1983 | Walrath et al. | 428/379 |
| 4,461,805 | 7/1984 | Walrath et al. | 428/349 |
| 4,496,715 | 1/1985 | Sattler | 528/288 |
| 4,501,883 | 2/1985 | Walrath et al. | 528/340 |
| 4,505,978 | 3/1985 | Smith | 428/379 |
| 4,505,980 | 3/1985 | Nishizawa et al. | 428/383 |
| 4,511,681 | 4/1985 | Yoshida et al. | 523/310 |
| 4,618,632 | 10/1986 | Su | 522/43 |

OTHER PUBLICATIONS

Rubner, R. et al, "Photoreactive Polyimide Precursors", Org. Coatings and Plastic Chemistry, 38(2) 125, (no date provided).

Primary Examiner—Mary C. Lee
Assistant Examiner—Jacqueline Haley
Attorney, Agent, or Firm—A. Mich, Jr.

[57] ABSTRACT

Solventless ultraviolet (UV) radiation curable polyamideimides which are useful as coatings for substrates are disclosed. The UV curable solventless polyamideimides are prepared by grafting acrylate functionality on the polyamideimide backbone The polyamideimides of the invention may be a part of UV curable compositions.

5 Claims, No Drawings

ULTRAVIOLET RADIATION CURABLE POLYAMIDEIMIDE OLIGOMERS

This application is a continuation of application Ser. No. 07/390,123 filed Aug. 7, 1989, now abandoned.

BACKGROUND OF THE INVENTION

1. Field of the Invention

The present invention relates to ultraviolet (UV) curable amideimide oligomers and associated ultraviolet curable resinous compositions that may be used as coatings on substrates.

2. The Prior Art

Polyamideimides are utilized in a wide range of commercial applications due to their unique combination of outstanding mechanical properties, excellent thermal stability, high glass transition temperature and good solvent resistance.

Polyamideimides can be made by the polycondensation reaction of an acid anhydride with a diamine. In that reaction, acid groups react with amine groups to produce amide groups, and anhydride groups react with amine groups to produce amic acid groups. The polyamideimide is then obtained by eliminating water from polyamic acid at high temperature (>200° C.) with or without catalysts (see, for example, U.S. Pat. No. 3,984,375). The water evaporation usually generates blisters and defects on the coating. While the blister problem can generally be solved by using a solution of very low solids content so that the polymer is applied as a very thin coating, this means that many passes are needed to build up an adequate coating thickness, which greatly increases the cost of the coating. Also, because the solvent used in the reaction is quite expensive and sometimes costs more than the monomers, a low solids amic acid solution is more expensive than a high solids solution In addition, the removal of solvent during the coating process generates volatile organic compounds emissions in the manufacturing environment.

Polyamideimides can also be made by the polycondensation reaction of an acid anhydride with a diisocyanate in polar solvents (see, for example, U.S. Pat. Nos. 3,518,230; 3,541,038; 3,578,639; 3,562,217; 3,732,186; 3,843,587; 4,069,209; 4,113,706; 4,379,879; 4,420,535; 4,461,805; 4,501,883; 4,505,978; 4,505,980; and, 4,511,681). In this reaction, the acid groups react with the isocyanate groups to produce amide groups and carbon dioxide, and the anhydride groups react with the isocyanate groups to produce imide groups and carbon dioxide. The polymer is preimidized and no volatiles, such as water or carbon dioxide, are evolved during cure. In this method, only the solvent must be evaporated. Thus, the use of diisocyanates to make polyamideimides seems more attractive than the use of amines. However, if the diisocyanate is used in equal or less than equal molar equivalents with the acid anhydride, a low molecular weight polymer and a brittle film results. If excess molar equivalents of diisocyanate are used, the composition has a poor shelf life and its viscosity increases rapidly. The solvent used in the preparation of the polymer still generates the volatile organic compounds emissions.

Therefore, there is a need for a solventless and 100% reactive amideimide oligomers which can be produced without solvent at low temperatures.

SUMMARY OF THE INVENTION

Polyamideimide oligomers and associated resinous compositions have been developed that are solventless and 100% reactive. In addition, UV curable compositions have been prepared using the polyamideimide oligomer of the present invention. These polyamideimide oligomers are prepared by grafting an acrylate functionality on the polyamideimide backbone. In one embodiment, trimellitic anhydride (TMA), toluene diisocyanate (TDI), and an acrylate containing a reactive hydrogen group are reacted through addition condensation polymerization to obtain an acrylated polyamideimide at low temperatures and without solvent. The polyamideimide oligomers can be cured by ultraviolet radiation without the emission of any volatile organic compounds.

It is an object of the present invention to provide polyamideimide oligomers that are solventless and that may be produced at low temperatures.

It is another object of the present invention to provide UV curable polyamideimides.

It is a further object of the present invention to provide a method of making the polyamideimides of the present invention.

It is yet another object of the present invention to provide compositions containing the polyamideimide of the present invention.

These and other objects of the present invention will be more fully understood from the following description of the invention.

DESCRIPTION OF THE PREFERRED EMBODIMENTS

The polyamideimide oligomers of the present invention are solventless and 100% reactive. These oligomers are prepared by grafting acrylate functionality on the polyamideimide backbone. The oligomer may be cured by ultraviolet radiation. This method provides polyamideimides at a low temperature of about 150° C. and no solvent, thereby eliminating the problems of the prior art.

The general structural formula of UV curable polyamideimide oligomers is shown as follows:

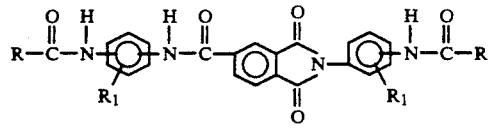

Where R is an aliphatic or aliphatic ester containing unsaturated hydrocarbon functionality, and $R_1$ is either hydrogen or an alkyl group ($C_1$ to $C_4$).

More preferably, R may be:

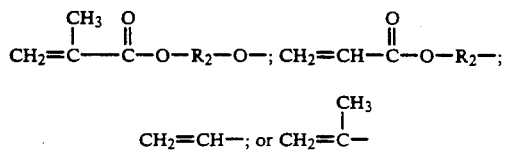

where $R_2$ is aliphatic hydrocarbon ($C_1$ to $C_{12}$) or aliphatic carboxylate ($C_1$ to $C_{12}$). When $R_1$ is an alkyl, it is preferably methyl.

Any aromatic acid anhydride, where both carboxylic acid and anhydride groups are on an aromatic ring, can be used in this invention. A preferred example of such an aromatic acid anhydride includes trimellitic anhydride (TMA). The mixtures of aromatic dicarboxylic acids, esters and aromatic dianhydrides can also be used in the reaction. Suitable compounds include terephthalic acid, isophthalic acid, trimellitic acid, 3,3',4,4'-benzophenone tetracarboxylic dianhydride, pyromellitic dianhydride, polyazelaic polyanhydride, pyromellitic tetracarboxylic acid, and alkyl esters of these acids The alkyl esters are preferably $C_1$ to $C_4$.

Any aromatic diisocyanate having both diisocyanate groups on an aromatic ring can be used in this invention. Examples include:
meta-phenylene diisocyanate
tolylene diisocyanate (also called "toluene diisocyanate")
dimethyl-3,3'-diisocyanato-4,4'-diphenylene
dimethoxy-3,3'-diisocyanato-4,4'-diphenylene
meta-xylylene diisocyanate
para-xylylene diisocyanate
bis (para-phenylene isocyanate)-oxadiazole-1,3,4
bis (meta-phenylene isocyanate)-oxadiazole-1,3,4
bis (meta-phenylene isocyanate)-4-phenyl-triazole-1,2,4
bis (4-paraphenylene isocyanate thiazole 2-yl) meta-phenylene
(2-phenylene)-benzimidazole 5,4'-diisocyanate
(2-phenylene)-benzoxazole 5,4'-diisocyanate
(2-phenylene)-benzothiazole 6,4'-diisocyanate
bis (2-phenylene isocyanate benzimidazole 6-yl) 2,5-oxadiazole-1,3,4
bis (para-phenylene isocyanate 2-benzimidazole 6-yl)
bis (para-phenylene isocyanate 2-benzoxazole 6-yl)
4,4'-diisocyanato diphenyl 2,2-propane
4,4'-diisocyanato diphenyl methane
4,4'-diisocyanato benzidine
4,4'-diisocyanato diphenyl sulfur
4,4'-diisocyanato diphenyl sulfone
4,4'-diisocyanato diphenyl ether
4,4'-diisocyanato diphenyl 1,1-cyclohexane oxides of methyl-and of bis (meta-isocyanato-phenyl) phosphine, and
diisocyanato 1,5-naphthalene.

The preferred aromatic diisocyanate is tolylene diisocyanate, as it is inexpensive and produces coatings having the best properties The preferred tolylene diisocyanate is a mixture of the 2,4- and the 2,6- isomers such as, for example, 80 mole % of the 2,4- isomer and 20 mole % of the 2,6- isomer, because such mixtures are less expensive.

Aromatic UV curable polyamideimides are preferred because they exhibit high temperature stability and good mechanical properties.

UV curable polyamideimides of the present invention may be obtained by the following oligomer preparations:

Oligomer I—Acrylated Urethane Amideimide Oligomers

Oligomer I may be prepared by reacting three moles of toluenediisocyanate (TDI) and two moles of trimellitic anhydride (TMA), then reacting the TDI-TMA adduct further with two moles of hydroxy terminated acrylate such as 2-hydroxy ethyl acrylate (HEA), 3-hydroxy propyl acrylate, 2-hydroxy methacrylate, hydroxy-ethyl-beta-carboxy ethyl acrylate, 3-hydroxy propyl methacrylate, hydroxy hexyl acrylate, hydroxy octyl methacrylate, 2-hydroxy propyl acrylate, 2-hydroxy ethyl methacrylate, and the like.

Oligomer I is prepared according to the following reaction:

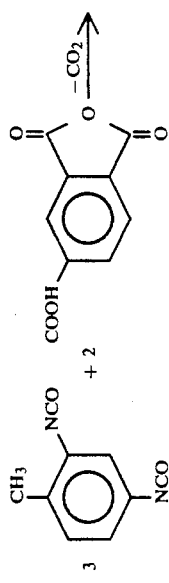
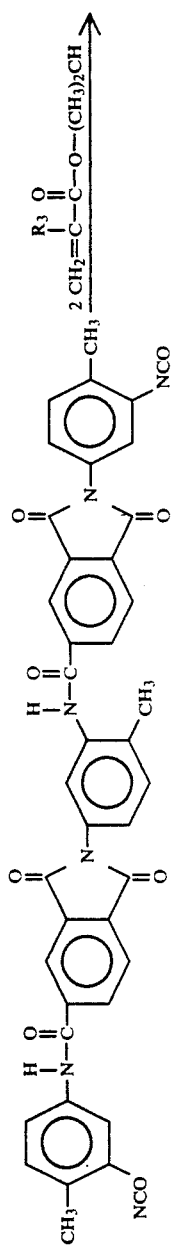
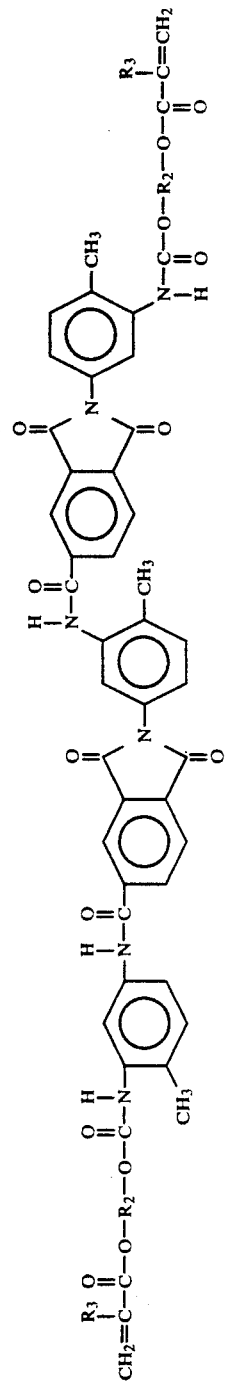

Oligomer II—Acrylated Amideimide Oligomers

Oligomer II—may be prepared by reacting two moles of TDI-TMA adduct with one mole of acrylic acid (AA).

The elimination of the urethane portion in Oligomer I by using acrylic acid (AA) instead of hydroxy terminated acrylate will improve the thermal stability of the Oligomer I.

Oligomer II is prepared according to the following reaction:

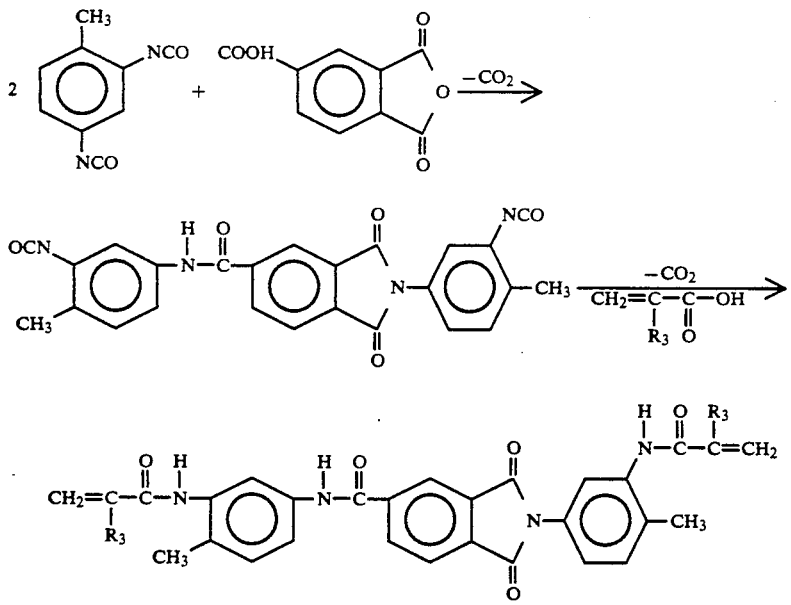

Oligomer III—Acrylate Amideimide Oligomers

The flexibility and solubility of Oligomer II may be improved by using a derivative of acrylic acid, such as β-carboxyethylacrylate (β-CEA) to react with the adduct of TMA and TDI; thus, Oligomer III is prepared by the method of Oligomer II and using β-CEA instead of AA.

Oligomer III is prepared according to the following reaction:

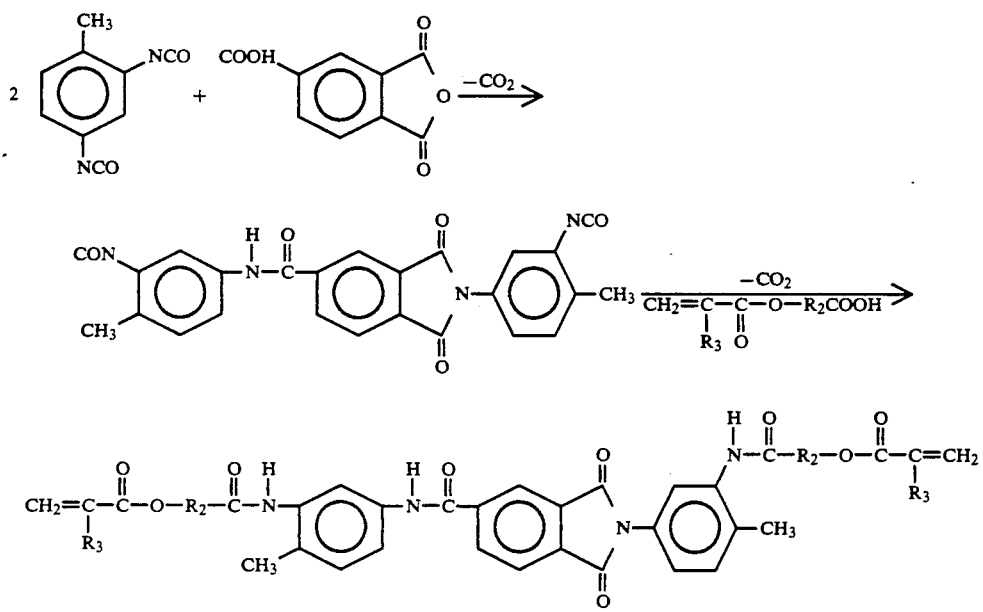

The molecular Weight of amideimide oligomer can be controlled by the stoichiometric of TDI and TMA adduct. For example, a lower molecular weight amideimide oligomer can be obtained by reacting one mole of TMA with two moles of TDI The photosensitivity of the oligomers depends on the number of acrylate functionality. For instance, the oligomer with more than one acrylate functionality on the backbone of the molecule will have a faster curing speed.

The amideimide oligomers are prepared from stoichiometrically balanced diisocyanates, acid anhydrides and acrylates containing an active hydrogen with about a 10% weight variation for each monomer.

An acrylate monomer such as phenoxy ethyl acrylate (PEA) is used in the preparation in an amount of about 20–50%, by weight to reduce the viscosity of oligomer and to increase the reaction rate. An inhibitor, such as benzoquinone, is used in the preparation in an amount of about 0.01–0.5%, by weight, to prevent gelation and to increase stability.

The polyamideimide of the present invention may be a component in various compositions. In a presently preferred embodiment, the polyamideimide may be a component in a UV curable composition. The UV curable composition may be a mixture of about 25 to 75 percent by weight of the polyamideimide of the present invention; about 20 to 74 percent by weight of a polyfunction acrylate monomer and about 1 to 5 percent by weight of a UV photoinitiator. Optionally, about 20 to 74 percent by weight of an acrylate epoxy may be added to the composition The acrylate epoxy used in a presently preferred composition of the invention is described in U.S. Pat. No. 4,481,258. Specifically, the acrylate epoxy is a reaction product of an epoxy resin and an acrylate adduct. The acrylate adduct is the reaction product of an acrylate which may be either 2-hydroxyethyl acrylate, 2-hydroxy propyl acrylate, 2-hydroxyethyl methacrylate or mixtures thereof, and an anhydride, which may be phthalic anhydride, maleic anhydride, trimellitic anhydride, or mixtures thereof.

Polyfunctional acrylate monomers include trimethylolpropane triacrylate (TMPTA), phenoxy ethyl acrylate (PEA), isobornyl acrylate, tetraethyleneglycol diacrylate (TEGDA), hexanediol diacrylate (HDDA), tripropylene glycol diacrylate, and mixtures thereof The preferred polyfunctional acrylate monomer is TEGDA.

The photoinitiator may be an ultraviolet curing substance but preferably is selected from benzoin ether derivatives, alpha-acryloxime derivatives, benzil ketal derivatives, acetophenone derivatives, ketone-amine combinations, onium salts, propanones, mixtures thereof, and the like.

Suitable benzoin ether derivatives include isobutyl benzoin ether (V-10 Stauffer Chemical), isopropyl benzoin ether, benzoin ethyl ether, and benzoin methyl ether.

Suitable alpha-acryloxime ester derivatives include 1-phenyl-1,2-propane-dione-2-(O-ethoxycarbonyl) oxime.

Suitable benzil ketal derivatives include 2,2-dimethoxy-2-phenyl-acetophenone (Irg 651, Ciba-Geigy), benzil, and hydroxy-cyclo-hexyl phenyl ketone.

Suitable acetophenone derivatives include diethoxyacetophenone and 2-hydroxy-2-methyl-1-phenylpropane-1-one.

Ketone-amine combinations include primary or secondary aliphatic and aromatic amines and the ketones include benzophenone, chlorothioxanthone, 2-chlorothioxanthone, isopropyl thioxanthone, 2-methylthioxanthone, chlorine functional substituted benzophenone, and halogen substituted alkyl-arylketone.

Suitable onium salts include iodonium salts, sulfonium salts, diazonium salts and thiopyrylium salts. A preferred sulfonium salt includes triaryl sulfonium hexafluorophosphate (FX-512; 3M).

Suitable propanones include 2-methyl-1-[4-(methylthio)phenyl-2-morpholino-propanone-1 (Irg 907, Ciba-Geigy).

Benzoin derivatives and benzil ketal derivatives are preferably used to cure resins having unsaturation. Onium salts are preferably used to cure resins having ring structures.

The composition may also optionally include a flow control agent. The flow control agent is preferably present in an amount of up to about 0.1%, by weight. The flow control agent is preferably a fluorohydrocarbon.

Other additives may be added to the composition such as coupling agents, adhesion promoters, dyes, pigments, fillers, and the like. These additives are preferably present in an amount of up to 10%, by weight, and more preferably about 0.1% to about 1%, by weight.

Coupling agents improve the adhesion of the coating on substrates, and especially optical fibers. Suitable coupling agents include acrylate silane (Z-6032, Dow Corning).

Adhesion promoters improve adhesion on substrates, and especially wire. Colorants, such as dyes or pigments, add color to the coating for easy identification. Fillers improve the toughness of the coating and flow control of the coatings. Suitable fillers include silicon oxide, zinc oxide and mixtures thereof.

Table 1 lists certain compositions containing the UV curable polyamideimide formulations of the present invention. The compositions use Oligomer I (R12054F).

TABLE 1

THE COMPOSITIONS OF THE UV CURABLE POLYAMIDEIMIDE FORMULATIONS

| Formulation | Composition*, Weight %/Component Name |
|---|---|
| R12054F-3 | 64.1/R12054F, 32.05/TEGDA, 3.85/Irg907 |
| R12054F-4 | 32.05/R12054F, 32.05/R10736, 32.05/TEGDA, 3.85/Irg651 |
| R12054F-5 | 48.5/R12054F, 24.27/R10736, 24.27/TEGDA, 3.85/Irg651 |
| *TEGDA: | Tetraethylene glycol diacrylate |
| Irg-651: | 2,2-dimethoxy-2,phenyl-acetophenone, Ciba Geigy |
| Irg-907: | 2-methyl-1-[4-(methylthio)phenyl]-2-morpholino-propanone-1, Ciba Geigy |
| R10736: | Acrylate bisphenol A epoxy, described in U.S. Pat. 4,481,258 |

Table 2 lists the coating properties of the formulations of Table 1. The coatings were applied on an aluminum Q-panel by Bird applicator in a thickness of 2 mil, then cured with Fusion Systems F(40) D bulb for the desired time.

TABLE 2

PROPERTIES OF UV CURABLE POLYAMIDEIMIDE COATINGS

| Formulation | Cure Speed Secs | Pencil Hardness | Crosshatch Adhesion, % |
|---|---|---|---|
| R12054F-3 | 10 | 2H | 93 |
| R12054F-4 | 10 | 2H | 94 |
| R12054F-5 | 20 | 3H | 100 |

As shown in Table 2, the UV curable polyamideimides have good adhesion, good hardness, and fast cure speed. The UV curable polyamideimides can be used as high temperature materials for the applications in wire coating, laminates, and composites. Because of the amideimide moiety in these new formulations, they exhibit better thermal stability than those of epoxy, polyester, or urethane based UV curable formulations. The UV curable polyamideimides, also have the advantages over the conventional thermal cured polyamideimide that they can be cured very rapidly and do not have any volatile organic emissions.

EXAMPLES

Preparation of UV Curable Amideimide Oligomers, R12054F (see Table 1)

A one liter reaction flask equipped with stirrer, thermometer, nitrogen sparge, and heating mantle was charged with 96 grams of trimellitic anhydride, 284.5 grams of phenoxy ethyl acrylate, and 1.3 grams of benzoquinone. The reactants were heated at 60° C. for one hour. A first part of 87 grams of toluene diisocyanate (80% 2,4 and 20% 2,6) was slowly added into the reaction mixture at a temperature of about 60° C. The reaction was carried out at about 120°-125° C. until the reaction mixture became clear (about 12 hours). The reaction mixture was cooled to 60° C., then the second part (43.5 grams) of the TDI, was added into the flask. The reaction was continued at 120°-125° C. for about 7 hours and the reaction mixture was cooled to about 60° C. Hydroxyethyl acrylate (116 grams) was added into the flask and reacted at about 120° C. for about 2 hours. A dark brown resin was obtained.

The infrared spectrum of resin showed all of the TDI was reacted and very strong amideimide absorptions at 1780 and 1720 cm$^{-1}$ were observed.

Preparation of R10736 Oligomer (see Table 1)

The reaction took place in a 600 ml stainless steel beaker, equipped with stirrer, thermometer, and heating mantle. The beaker was charged with 192.1 grams of trimellitic anhydride, 116.1 grams of hydroxyethyl acrylate and 2.6 grams of benzoquinone. The reactants were heated to 120° C. for about 1.5 hours.

A five-liter reaction flask equipped with stirrer, thermometer, nitrogen sparge, and heating mantle was charged with 66.0 grams of the above material, along with 1753.0 grams of a bisphenol A epoxy resin with an epoxy equivalent weight of about 2000, 1819 grams of phenoxyethyl acrylate and 1.71 grams of triethanolamine. The reactants were heated to 140°-150° C. for about 1.5 hours to an acid number below 5. A viscous resin was obtained.

Preparation of UV Curable Polyamideimide Compositions (See Table 1)

The polyfunctional acrylate monomer, photo-initiator, polyamideimide and optional additives were mixed with the oligomer at room temperature to obtain the polyamideimide compositions of the present invention.

It will be appreciated that the above-described invention provides novel polyamideimides, a method of making them, and ultraviolet curable compositions containing these novel polyamideimides. The polyamideimides of the present invention display superior thermal stability and may be used as high temperature materials. The polyamideimide composition may be rapidly UV cured without volatile organic emissions.

Whereas particular embodiments of the invention have been described above for purposes of illustration, it will be appreciated by those skilled in the art that numerous variations of the details may be made without departing from the invention as described in the appended claims.

What we claim is: What we claim is:
1. A compound having the general formula:

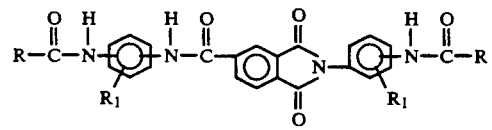

where R is selected from the group consisting of

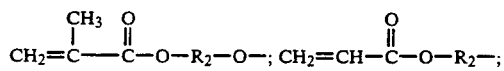

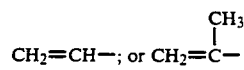

where $R_2$ is alkyl or alkenyl ($C_1$ to $C_{12}$) and $R_1$ is hydrogen or alkyl ($C_1$ to $C_4$).

2. The compound of claim 1 where R is

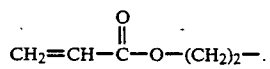

3. The compound of claim 1 where R is

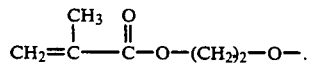

4. The compound of claim 1 where R is $CH_2=CH-$.
5. The compound of claim 1 where R is

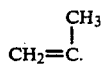

* * * * *